(12) United States Patent  
Reisfeld

(10) Patent No.: US 6,833,122 B2  
(45) Date of Patent: Dec. 21, 2004

(54) COMBINED PARTICLE FILTER AND PURIFIER

(75) Inventor: Brad Reisfeld, Fort Collins, CO (US)

(73) Assignee: Carrier Corporation, Farmington, CT (US)

( * ) Notice: Subject to any disclaimer, the term of this patent is extended or adjusted under 35 U.S.C. 154(b) by 318 days.

(21) Appl. No.: 10/103,097

(22) Filed: Mar. 20, 2002

(65) Prior Publication Data

US 2003/0180200 A1 Sep. 25, 2003

(51) Int. Cl.$^7$ .......................... B01J 19/12; B01D 59/12
(52) U.S. Cl. ........................ 422/186.3; 96/4; 96/224; 96/225
(58) Field of Search ................ 422/186.3; 96/4, 96/224, 225

(56) References Cited

U.S. PATENT DOCUMENTS 5,109,916 A * 5/1992 Thompson ................... 165/59
5,564,065 A * 10/1996 Fleck et al. ............. 422/186.3

* cited by examiner

Primary Examiner—Steven Versteeg
(74) Attorney, Agent, or Firm—Wall Marjama & Bilinski LLP

(57) ABSTRACT

A heating and cooling system which includes in combination a blower, a hot air furnace and an air conditioner unit with interconnected ducting and a filter/purification member positioned on the upstream side of the blower. The filter/purification member functions to mechanically filter solids with the purification component functioning to act as a catalyst for UVPCO when exposed to ultraviolet light. The filter is a mechanical filter which further contains a titania component and a source of UV light adjacent the filter to facilitate UVPCO.

4 Claims, 2 Drawing Sheets

COMBINED PARTICLE FILTER AND PURIFIER

BACKGROUND OF THE INVENTION

The present invention broadly relates to a filter for an air conditioner and heating system and more specifically to a combined mechanical particle filter and purifier element.

Three important considerations in providing for indoor air quality are airborne particles, gas phase pollutants and airborne microbes. Mechanical filtration is conventionally used to remove particles from the air. Ultraviolet photocatalytic oxidation (UVPCO) purification can remove gas phase pollutants, such as formaldehyde, and also function to destroy a large fraction of airborne microbes. Providing a system which is designed to address all of these three airborne problems presents a challenge in the field with respect to the size, complexity and cost associated with both the filtration and purification functions. It therefore can be seen that there is a need in the field of residential heating and cooling, for a system which can remove both particles from the air and effectively provide for the removal of gas phase pollutants and airborne microbes while meeting the objectives of reduced sized and low cost.

SUMMARY OF THE INVENTION

It is therefore an object of the present invention to provide a filter system which overcomes the problems of the prior art described above.

It is a further object of the present invention to provide a combination of a mechanical filtration system with ultraviolet photocatalytic air purification which can be used in a residential heating and air conditioning system.

It is a further object of the present invention to provide a combination of mechanical filtration and purification which effectively removes solid particles, gas phase pollutants and airborne microbes from an air stream.

The present invention is directed to a combination of a filter media and purification system which effectively removes solid particles, gas phase pollutants and airborne microbes by combining the mechanical filtration and ultraviolet photocatalytic oxidation functions into a single member which is positioned in a predetermined location in a residential heating and air conditioning system. More specifically the device employs a mechanical filter media that is coated with or contains a titania (titanium dioxide $TiO_2$) component. The mechanical filtration portion of the device effectively filters solid particles from the air. The source of UV radiation is associated and placed adjacent the filter purification member. Ultraviolet light promotes ultraviolet photocatalytic oxidation (UVPCO) purification which effectively removes gas phase pollutants and airborne microbes. The coarseness and nature of the filter can be adjusted to balance the mechanical filtration efficiency with the desired pressure drop characteristic. The characteristic of the filter can also be adjusted to optimize the loading of the titania catalytic. Once exposed to ultraviolet light the filter through the titania acts as a catalyst for UVPCO. Once the filter has trapped a recommended amount of particles, it can either be washed or disposed of depending on the filter cost and material, and the type of system in which it is employed.

BRIEF DESCRIPTION OF THE DRAWINGS

For a further understanding of these and objects of the invention, reference will be made to the following detailed description of the invention which is to be read in connection with the accompanying drawings, wherein.

DETAILED DESCRIPTION OF THE INVENTION

Figure 1:
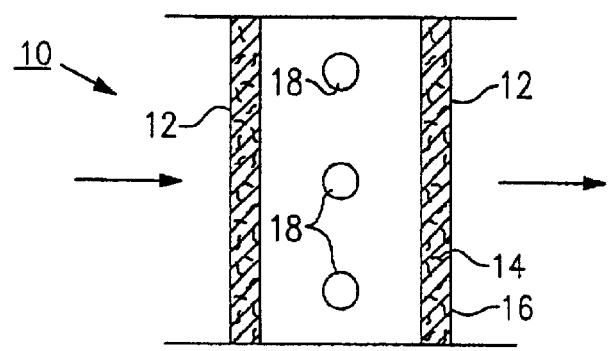
FIG. 1 is a side schematic view of one embodiment of the invention utilizing two filter members.
Figure 5:
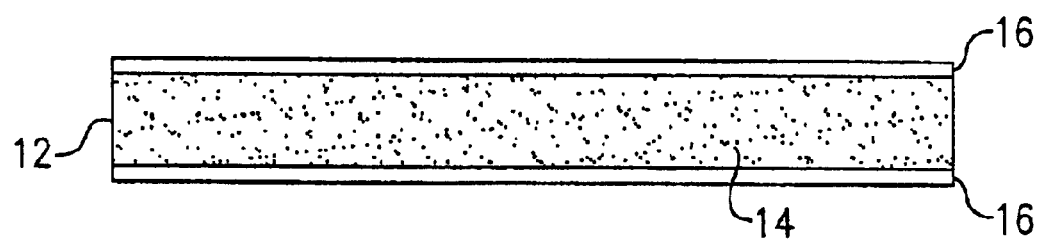
FIG. 5 is an enlarged view of a titania coating on the surface of a filter media.
Figure 6:
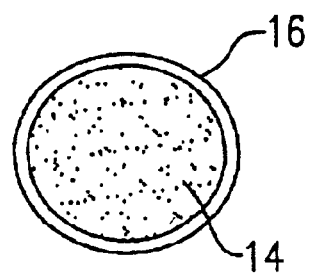
FIG. 6 is a view of a fiber of filter media coated with titania.

The present invention is more fully understood with reference to the drawings wherein FIG. 1 represents one embodiment of the present invention. The arrows in the drawings represent the direction of the air flow. In FIG. 1 the air filter/purification unit 10 of the present invention is illustrated by two identical filter means 12 which comprise a filter member 14 typically in the form of interlocking fibers 14. The fibers may be coated with catalyst titania ($TiO_2$) or titania can be coated onto the surface or impregnated onto the surface of the filter media. FIG. 5 is an enlarged view and illustrates a titania coating 16 on the surface of the filter. In FIG. 6 the fibers 14 of the filter have been coated with the titania 16. A plurality of UV lights 18 are positioned adjacent filters 12.

For residential systems the typical cross sectional dimensions for the filter can be 16×20 inches; 20×24 inches or 20×20 inches. The thickness of the filter typical is around 0.75 inches however higher efficiency filters can range from 2 to 6 inches in depth. The filter may comprise any typical mechanical filtering material such as fiberglass, plastics such as polyester, other dry materials and metals. Materials can be in the form of the fibers, filament, strands, slit foils, plate structures or porous media structures.

Figure 2:
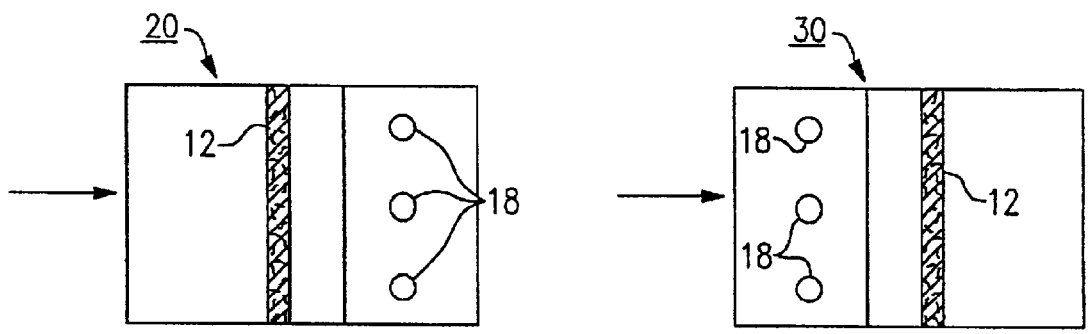
FIG. 2 is a schematic view of a second embodiment of the invention for a front loading filter where the dust tends to accumulate on the front side of the filter.

FIG. 2 illustrates a second embodiment of the invention 20 for a front loading type filter where the dust tends to accumulate on the front side of the filter.

Figure 3:
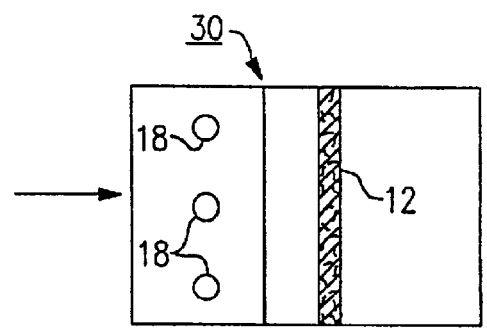
FIG. 3 is a schematic view of a further embodiment of the invention for a back loading filter where the dust tends to accumulate on the back side of the filter.

FIG. 3 illustrates a further embodiment 30 of the present invention for a back loading filter where the dust tends to accumulate on the back side of the filter.

Figure 4:
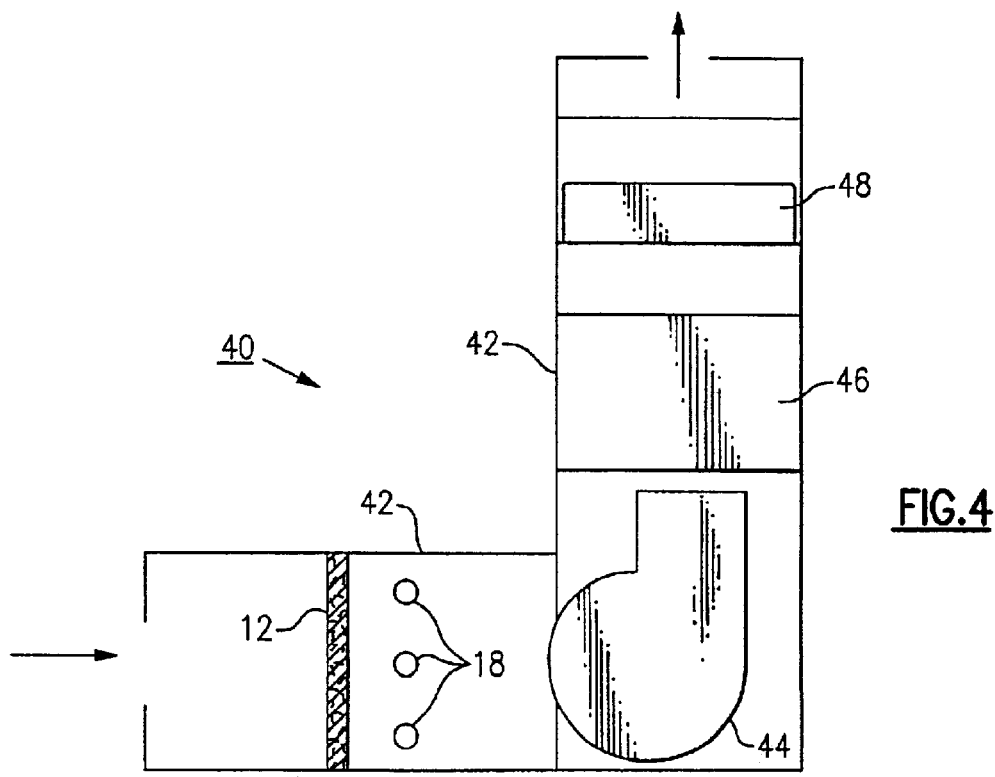
FIG. 4 is a schematic illustration of the residential heating and cooling system utilizing the filter purification member of the present invention.

FIG. 4 is a schematic illustration of the application of the present invention for use in a residential heating and cooling system 40 which has the appropriate ducting 42. A filter member 12 containing the titania (not shown) is positioned on the up flow side of the system with the UV lights 18 placed adjacent and on the down flow side of the filter. Blower 44 directs the flow of air to furnace 46 with cooling coils 48 being down stream of the furnace. In operation, the air flow through the filter results in a solid particles such as dust being filtered out by the filter media. When exposed to ultraviolet light, the filter acts as a catalyst through the $TiO_2$ for UVPCO. Once the filter has trapped the recommended amount of particles it can either be cleaned or disposed of depending on the system and the cost of the filter.

The following is a brief explanation of the mechanism of the catalytic or purification part of the system.

Titania or titanium dioxide ($TiO_2$) is a semiconductor photocatalyst with a band gap energy of 3.2 eV. When this material is irradiated with ultraviolet light (photons of less than 385 nm), the band gap energy is exceeded and an electron is promoted from the valence band to the conduction band. The resultant electron-hole pair has a lifetime in the space-charge region that enables its participation in chemical reactions. The most widely postulated reactions are shown here.

$$OH^- + h^+ \rightarrow OH$$

$$O_2 + e^- \rightarrow O_2^-$$

Hydroxyl radical and super-oxide ions are highly reactive species that will oxidize volatile organic compounds (VOCs) adsorbed on the catalyst surface. They will also kill and decompose adsorbed bioaerosols. The process is referred to a heterogeneous photocatalysis or, more specifically, ultraviolet photocatalytic oxidation (UVPCO).

Several attributes of UVPCO make it a strong candidate for indoor air quality (IAQ) applications. Pollutants, particularly VOCs, are preferentially adsorbed on the surface and oxidized to (primarily) carbon dioxide ($CO_2$). Thus, rather than simply changing the phase and concentrating the contaminant, the absolute toxicity of the treated air stream is reduced, allowing the photocatalytic reactor to operate as a self-cleaning relative to organic material on the catalyst surface.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A heating and cooling system which includes in combination a blower, a hot air furnace and an air conditioner unit with interconnected ducting and a unitized filter/purification member positioned adjacent said blower, with said filter/purification member comprising mechanical filtering means, a titania purification component and a source of UV light adjacent said member, with said filter/purification member functioning to mechanically filter solids and said purification component functioning to act as a catalyst for ultraviolet photcatalytic oxidation when exposed to ultraviolet light.

2. The system of claim 1 in which the unitized filter/purification member is positioned on the upstream side of the blower.

3. A unitized air filter purification unit suitable for use in a heating and cooling system which comprises a mechanical filter which contains a filter medium suitable for filtering solid particles from an air stream, said filter further containing a titania catalyst which upon exposure to ultraviolet light, acts as a catalyst for ultraviolet photocatalytic oxidation.

4. The unit of claim 3 in which the filter medium is coated or impregnated with the titania.

* * * * *